(12) United States Patent
Klem et al.

(10) Patent No.: US 10,874,875 B2
(45) Date of Patent: *Dec. 29, 2020

(54) IRRADIATION DEVICE

(71) Applicant: Photocure ASA, Oslo (NO)

(72) Inventors: Bjorn Klem, Oslo (NO); Morten Groseth, Oslo (NO)

(73) Assignee: PHOTOCURE ASA, Oslo (NO)

(*) Notice: Subject to any disclaimer, the term of this patent is extended or adjusted under 35 U.S.C. 154(b) by 0 days.

This patent is subject to a terminal disclaimer.

(21) Appl. No.: 15/362,112

(22) Filed: Nov. 28, 2016

(65) Prior Publication Data

US 2017/0072217 A1 Mar. 16, 2017

Related U.S. Application Data

(63) Continuation of application No. 13/595,167, filed on Aug. 27, 2012, now abandoned, which is a
(Continued)

(30) Foreign Application Priority Data

Jan. 12, 2009 (GB) .................................. 0900461.5
Sep. 22, 2009 (GB) .................................. 0916666.1

(51) Int. Cl.
*A61N 5/06* (2006.01)
*A61B 5/00* (2006.01)
(Continued)

(52) U.S. Cl.
CPC ............ *A61N 5/062* (2013.01); *A61B 5/0084* (2013.01); *A61K 9/0036* (2013.01);
(Continued)

(58) Field of Classification Search
CPC .............. A61N 5/062; A61N 5/0603; A61N 2005/0611; A61N 2005/0608;
(Continued)

(56) References Cited

U.S. PATENT DOCUMENTS 4,858,624 A   8/1989   Shihata
5,445,608 A   8/1995   Chen et al.
(Continued)

FOREIGN PATENT DOCUMENTS

CN   101293124 A   10/2008
DE   296 11 520 U1   9/1996
(Continued)

OTHER PUBLICATIONS

Allison, R. R., et al., "PD/PDT for gynecological disease: A clinical review", Photodiagnosis and Photodynamic Therapy; (2005); vol. 2, pp. 51-63.
(Continued)

*Primary Examiner* — Jennifer Pitrak McDonald
*Assistant Examiner* — Elizabeth K So
(74) *Attorney, Agent, or Firm* — Fox Rothschild LLP

(57) ABSTRACT

An irradiation device for insertion into an orifice of the body for providing photodynamic therapy or diagnosis comprises: a housing 1, 21, 31, 51, 61, 71 adapted to be fully inserted and secured in the orifice, the housing 1, 21, 31, 51, 61, 71 enclosing an LED lamp system 5, 25, 35, 45, 54, 62, 72 and a power source 41, 68, 78, for powering the LED lamp system 5, 25, 35, 45, 54, 62, 72, wherein the device is independently operational while located within the orifice.

16 Claims, 6 Drawing Sheets

Related U.S. Application Data continuation of application No. 13/144,222, filed as application No. PCT/EP2009/009037 on Dec. 16, 2009, now abandoned.

(51) Int. Cl.
  *A61K 9/00* (2006.01)
  *A61K 31/221* (2006.01)
  *A61K 41/00* (2020.01)

(52) U.S. Cl.
  CPC ........ *A61K 31/221* (2013.01); *A61K 41/0061* (2013.01); *A61N 5/0603* (2013.01); *A61N 2005/0608* (2013.01); *A61N 2005/0611* (2013.01); *A61N 2005/0626* (2013.01); *A61N 2005/0645* (2013.01); *A61N 2005/0652* (2013.01); *A61N 2005/0658* (2013.01)

(58) Field of Classification Search
  CPC .... A61N 2005/0652; A61N 2005/0645; A61B 5/0084; A61K 31/221; A61K 9/0036
  USPC .............................................. 607/88–92, 138
  See application file for complete search history.

(56) References Cited

U.S. PATENT DOCUMENTS

| | | |
|---|---|---|
| 5,674,239 A | 10/1997 | Zadini et al. |
| 6,034,267 A | 3/2000 | Gierskcky et al. |
| 8,057,464 B2 | 11/2011 | Chen et al. |
| 8,292,935 B2 | 10/2012 | Neuberger et al. |
| 9,974,974 B2 * | 5/2018 | Groseth ............ A61N 5/0603 |
| 10,485,985 B2 * | 11/2019 | Groseth ............ A61N 5/0603 |
| 2003/0097122 A1 | 5/2003 | Ganz et al. |
| 2004/0043349 A1 | 3/2004 | Liao |
| 2004/0259949 A1 | 12/2004 | Klaveness et al. |
| 2005/0104059 A1 | 5/2005 | Friedman et al. |
| 2005/0239018 A1 | 10/2005 | Green et al. |
| 2006/0136013 A1 | 6/2006 | Sherman |
| 2006/0293645 A1 * | 12/2006 | Hibner ................ A61B 5/0084 606/13 |
| 2007/0167999 A1 * | 7/2007 | Breden ................ A61N 5/06 607/88 |
| 2007/0259310 A1 | 11/2007 | Goodson et al. |
| 2007/0260231 A1 | 11/2007 | Rose et al. |
| 2007/0260295 A1 | 11/2007 | Chen et al. |
| 2008/0065003 A1 | 3/2008 | Neuberger et al. |
| 2009/0198173 A1 | 8/2009 | Samuel et al. |
| 2009/0319008 A1 | 12/2009 | Mayer |
| 2011/0190689 A1 | 8/2011 | Bennett et al. |

FOREIGN PATENT DOCUMENTS

| | | |
|---|---|---|
| DE | 10 2006 001 736 A1 | 7/2007 |
| EP | 1 138 349 A2 | 10/2001 |
| GB | 2360461 A | 9/2001 |
| GB | 2366734 A | 3/2002 |
| GB | 2370992 A | 7/2002 |
| JP | 50-19744 Y | 6/1975 |
| JP | 58-010067 A | 1/1983 |
| JP | 2002-065875 A | 3/2002 |
| WO | 1993-012836 A1 | 7/1993 |
| WO | 96/23543 A1 | 8/1996 |
| WO | 1996/028412 A1 | 9/1996 |
| WO | 1998-046130 A1 | 10/1998 |
| WO | 1999-019024 A1 | 4/1999 |
| WO | 2001-087416 A1 | 11/2001 |
| WO | 2002/09690 A1 | 2/2002 |
| WO | 2002/010120 A1 | 2/2002 |
| WO | 2003/011265 A2 | 2/2003 |
| WO | 2003-033067 A2 | 4/2003 |
| WO | 2004-082736 A2 | 9/2004 |
| WO | 2004-096074 A2 | 11/2004 |
| WO | 2005-092838 A1 | 10/2005 |
| WO | 2006/051269 A1 | 5/2006 |
| WO | 2006-103678 A2 | 10/2006 |
| WO | 2007-127894 A2 | 11/2007 |
| WO | 2007-130072 A2 | 11/2007 |
| WO | 2008-021692 A2 | 2/2008 |
| WO | 2008-084241 A2 | 7/2008 |
| WO | 2010/026422 A1 | 3/2010 |

OTHER PUBLICATIONS

Extended European Search Report dated Feb. 26, 2013 in EPO Divisional Patent Application No. 12188421.7 (Published as EP 2 545 962 A2), filed on Dec. 16, 2009.

Keefe, Kristin A., et al., "Photodynamic Therapy of High-Grade Cervical Intraepithelial Neoplasia With 5-Aminolevulinic Acid", Lasers in Surgery and Medicine, (2002); vol. 31, pp. 289-293.

Office Action from Japanese Patent Application No. 2011-544801 dated Mar. 5, 2013 (with English translation).

Soergel, et al ; "Photodynamic Therapy of Cervical Intraepithelial Neoplasia With Hexaminolevulinate"; Lasers in Surg. Med. (2008); vol. 40; pp. 611-615.

Jaques, S. L. et al., "PDT with ALA/PPIX is Enhanced by Prolonged Light Exposure Putatively by Targeting Mitochondria", SPIE Proceedings, (1997); vol. 2972; 6pgs.

Seshadri, M. et al., "Light Delivery over Extended Time Periods Enhances the Effectiveness of Photodynamic Therapy" Clinical Cancer Res. (2008); vol. 14:9; pp. 2796-2805.

* cited by examiner

IRRADIATION DEVICE

This invention relates to an irradiation device for insertion into an orifice of the body for providing photodynamic therapy or diagnosis of diseases, lesions and conditions thereof.

An example of an orifice of the body where photodynamic treatment is of benefit is the female reproductive tract. Conditions affecting the female reproductive tract are discussed below. Similar conditions, or conditions that respond to similar treatments, can arise in other orifices, such as the rectum, ear or nose.

The human papillomavirus (HPV) is a virus that can infect the skin and mucus membranes in humans. More than 100 different types of HPV have been identified. Several HPV types are transmitted through sexual activity and are pathogenic. HPV is estimated to be the most common sexually transmitted infection in the US. Several hundred million women worldwide are infected with HPV once in their life-time (~70%), with the highest prevalence, 20-30%, occurring in young women. These viruses can cause infections in the female genitalia and result in female genitalia diseases like genital warts, dysplasia and cervical cancer.

Cervical cancer is a life-threatening disease and is today the third most common cancer form among women world wide. Scientists agree that there is a strong correlation between the development of cervical cancer and HPV. Persistent HPV infection of the cervix may induce cell abnormalities including cervical intraepithelial neoplasia (CIN), precancerous lesions, and ultimately cervical cancer.

Fortunately mild cellular abnormalities including CIN1 have a high degree of spontaneous regression (>60%), and this is a condition that is normally only followed up by colposcopy. Moderate to severe CIN (CIN2 and CIN3) have a lower degree of spontaneous regression and a higher risk of progression. Patients with CIN2 and CIN3 are therefore conisized, usually by surgical procedures including diathermia, laser conisation and hysterectomy. The efficacy is about 90%, but side effects are disturbing, causing increased risk of bleeding, infection, stenosis, infertility and preterm labour.

If not treated, the precancerous cells will progress into more severe forms like carcinoma and neuroendocrine carcinoma. Treatment methods for cervical cancer are, as with most other cancer forms, dependent on the development stage of the disease. Treatment of early stage cervical cancer is normally various forms of surgery, while late stage cervical cancer is treated with surgery in combination with radiation therapy and chemotherapy. The most common chemotherapy of cervical cancer includes use of cisplatin. It is estimated that around 11,000 women a year will be diagnosed with cervical cancer, and that almost 4,000 will die from the disease. The degree of survival (over 5 years) depends on the stage of the disease and is, on average, above 50%.

Photodynamic therapy (PDT) is a therapeutic modality using a combination of light and a photosensitizer. When illuminated at a suitable wavelength the photosensitizer or "PDT drug" reacts with tissue oxygen to form oxygen radicals that interact with cellular organelles including the mitochondria and cell membranes. These interactions cause cell necrosis or apoptosis (programmed cell death). PDT is today used clinically for the treatment of several diseases, including various skin diseases.

Typical products for use in skin PDT are Metvix® (Galderma, Switzerland) and Levulan® (Dusa Pharmaceuticals Inc, Wilmington, USA).

A range of photosensitizers are known from the scientific literature. One type of such compounds is per se toxic to target cells or species or have light emitting properties when exposed to light. Such compounds have a relatively large molecular weight and are often complex molecules like phthalocyanines, chlorines, porphyrins and psoralens. Another, more clinically useful, type of compound are photosensitizer precursors that per se are not phototoxic or light emitting, but form photo-active compounds, e.g. endogenous porphyrins, in vivo. Such compounds are typically 5-aminolevulinic acid (5-ALA) and derivatives of 5-ALA like 5-ALA esters, and will be referred to hereafter as "precursors".

There is currently no product on the market for PDT or diagnosis of diseases, lesions or conditions of the cervix. However, there are several scientific reports on clinical research related to PDT of the cervix including PDT of human papillomavirus infections.

In a recently published study (P. Soergel et al, Lasers in Surgery and Medicine 40:611-615 (2008)), 24 patients with a CIN2 or CIN3 or a persistent CIN1 received local application of 5-ALA hexylester in a thermogel formulation. The patients were advised to stay supine for the next 3-5 hours before illumination which was performed for 17 minutes with a laser at a high light dose of 100 J/cm$^2$. At 2-3 months later, the clinical effect was assessed, and a second PDT treatment was offered for individuals with an incomplete response to the first PDT. All patients were scored at 6 months after the first treatment, and a complete response rate of 63% was found.

It is evident from the above that this is a time-consuming treatment both for the patients and for the gynaecologists. The patients will have to visit the gynaecologist to have the formulation applied, they then have to stay supine for 3-5 hours and then to visit the gynaecologist again for illumination. In addition, many of the patients who did not respond to the first treatment and had to go through the procedure once more.

The overall conclusion from these studies is that there is room for improvement in the clinical treatment efficacy of PDT in treating HPV and cervical cellular abnormalities. Furthermore, the procedure is time-consuming both for the patients as well as for the hospital personnel. Similarly, there is room for improvement in the treatment of other conditions affecting the female reproductive tract and in the treatment of conditions affecting other orifices.

There are several patent documents describing various devices for vaginal use, cervical drug delivery or photo-related diagnosis or therapy.

US 2008/0065003 discloses a LED-based cervical PDT device comprising an illumination head to be inserted into the cervical region. An LED array is either placed within the illumination head or in a hand piece connected to the head via a light guide. The device is connected to an external power supply and the light emitted by the LEDs is directed onto the cervix by a spherical reflector within the illumination head.

GB 2370992 discloses an LED PDT device for treatment of the cervix. This consists of a head portion containing an LED array which is shaped for insertion through the vagina to fit closely over the opening of the cervix. The head portion is connected to a hand piece via a hollow stem, through which air and power are supplied from an external air and power supply to the LED array. The device is clamped into position for the duration of the treatment.

As will be appreciated, both of these devices require operation by a medical practitioner and so will normally be used within a medical institution, such as a hospital or GP surgery. The patient must remain still during the length of the illumination, which is inconvenient and limits the practical length of each treatment session.

In addition, the photosensitizer must be applied to the cervical area prior to use of the device. It is usual with current methods for the patient to wait several hours between application of the photosensitizer/precursor and illumination.

PDT is today not a clinically valuable method for therapy of CIN and other diseases/conditions of the cervix. This is due to the ineffective results of therapy, as outlined in the above cited report. Thus, there is a need for improved methods for therapy of the cervix organ system.

Surprisingly, it has been found by the inventors of the present invention that the use of a specific device, in combination with a photosensitizer or precursor, improves therapy of cervical cancer and other cervical diseases, lesions and conditions, especially those diseases, lesions and conditions caused by HPV infection. Similar improvements can be made in connection with photodynamic treatment of other conditions affecting the female reproductive tract like for instance vulvar intraepithelial neoplasia (VIN) or vulvar carcinomas. Further, similar improvements can be made in connection with PDT of cancerous or precancerous conditions or lesions of any other orifice of the human or animal body.

According to one aspect the present invention provides an irradiation device for insertion into an orifice of the body for providing photodynamic therapy or diagnosis, the device comprising: a housing adapted to be fully inserted and secured in the orifice, the housing enclosing an LED lamp system and a power source for powering the LED lamp system, wherein the device is independently operational while located in the orifice.

Unlike prior art devices, the device of the present invention does not require the patient to remain at a medical facility during treatment. Rather, use of the device will often imply only one visit to the medical facility, after which the patient is free to leave. Prolonged ongoing treatment can occur while the patient continues with his or her normal daily activities.

This is because the device is adapted to be fully inserted and secured in the orifice and does not require connection to an external power supply or light source during operation. By "independently operable" it is meant that the device can provide illumination for PDT without concurrent connection to any external device. The device is hence fully self-contained and forms an enclosed unit including both the light source and the power supply required for photodynamic procedures.

As well as increasing the comfort and minimising disruption to the patient, another advantage of the present invention is that illumination can occur is preferably carried out at very low fluence rates. Fluence rate, F, refers to the radiant power incident on a unit area and is measured in units of $W/cm^2$. Illumination with low fluence rates (e.g. 10 $mW/cm^2$) requires that the illumination will have to occur over a relatively long time period, e.g. many hours, in order to achieve the desired light dose necessary to achieve a therapeutic effect, and hence is impossible in a clinical (hospital) situation. However, illumination using low fluence rates is known to strongly reduce the patient discomfort (pain) during illumination, and may also improve the PDT effect by allowing a continuous build-up of endogenous porphyrins (from precursors) and to prevent oxygen depletion during illumination (S. Jacques et al., "PDT with ALA/PPIX is enhanced by prolonged light exposure putatively by targeting mitochondria", SPIE Proceedings Vol. 2972, "Optical Methods for Tumor Treatment and Detection", ed. T. Dougherty, San Jose, February 1997, and M. Seshadri et al., Clin Cancer Res 14(9), 2796-2805 (2008)).

The device is therefore not only more "patient friendly", it can also increase the efficacy of the treatment.

The shape of the housing can vary, but is generally designed so that it comfortably fits within the orifice and remains in place independent of the patient's physical activity. Where the orifice of interest is the female reproductive tract, suitable shapes for the outer portion of the housing can for example be similar to the shapes of some contraceptive devices used to prevent pregnancy, such as FemCap® and other similar devices intended for blocking sperm from entering the uterus. For other orifices, other suitable shapes and structures can be utilised, for example based on shapes known for use as suppositories and/or pharmaceutical pessaries.

Although the present invention has been created with the treatment of human patients in mind, it is also possible for the device to be used in the treatment of other animals. Therefore the shape of the housing will be dependent on the orifice where treatment is required and on the anatomical structure of the animal on which the device is intended for use.

The device can comprise a slim housing, which the walls of the orifice will envelope and hold in place. When the device is for vaginal use the housing may, for example, be similar in size and shape to a tampon. The outer surface of the housing may be textured to improve the grip of the device. A textured surface can also be of benefit in providing a surface for the delivery of drugs to the area of the body that requires treatment.

To ensure a comfortable and effective treatment for each patient, devices of different sizes and/or shapes may be made available. For example, in the case of treatment of the cervix devices of three size may be provided for (i) patients that have not been pregnant, (ii) patients that have had a pregnancy but not carried to term and (iii) patients who have given birth.

For some orifices, for example the rectum, a simple 'torpedo' shape will enable the device to be inserted and secured. However, for other applications additional features may be present in order to ensure that the device is securely held within the orifice during use. Hence, for vaginal use the housing preferably comprises a flexible outer portion that can adjust its shape to form a secure fit with the vaginal walls and enables the device to be used within many different shapes and sizes of vagina. The flexible outer portion also helps to decrease the risk of slipping or misalignment of the device over an extended treatment period, during which the patient may be physically active. A similar outer portion may be used for a device intended for insertion in other orifices, if required.

For insertion into the ear or nose the device may be shaped based on known designs for ear or nose plugs.

The flexible outer portion can be formed from any material capable of adjusting its shape. For example, the flexible portion may be formed of an expandable, compressible or deformable material. A housing at least partially comprised of deformable material could adjust its shape during insertion to conform to the diameter of the orifice. Alternatively an expandable material could be used such that, after insertion, the outer portion of the housing expands to firmly grip the walls of the orifice. The expansion could be initiated through body heat, exposure to fluid, removal from a delivery device/instrument etc.

Preferably however the flexible outer portion is formed of a resilient material. This enables the shape of the flexible portion to be altered while also providing a biasing outwards force to hold the device in place. In order to achieve this effect the outer diameter of the outer portion should be sized such that this must be reduced in order to insert the device into the orifice. The outer portion will then provide an outwards force to the walls of the orifice.

The resilient material can be any resilient material commonly used in medical devices; for example rubber, latex, silicone or other natural, semi-synthetic or synthetic polymers or copolymers.

The flexible outer portion can be any shape which is capable of creating a secure fit with the walls of the orifice. For example, the flexible outer portion may be provided in the form of a number of discrete legs, ridges or other protrusions radially and/or longitudinally spaced about and extending outward from the housing. In other embodiments the flexible outer portion may form a continuous outer surface of the housing. This surface could either form the whole or a part of the exterior of the housing. For example the outer portion may be a disk or cup-shaped section found at either the front or rear of the device, or a covering which extends over the entire length of the housing.

In a preferred embodiment the flexible outer portion forms a continuous surface which tapers outwards towards the rear end of the device i.e. the end of the device which, in use, is closest to the entrance of the orifice. For example the outer portion can be approximately frustoconical in shape.

Although it is only necessary for an outer portion of the housing to be flexible, in certain preferred embodiments the entire housing is flexible. Creating a device having a flexible housing increases the comfort of the device and eases construction as only a single material is required.

Preferably the housing comprises a treatment surface, the LED system being arranged to emit radiation from the treatment surface. The device can be arranged to provide irradiation to the walls of the orifice, in which case the treatment surface may be an outer circumferential surface of the housing. The treatment surface preferably has a size and or shape selected for complimentary fit with the treatment area, and is preferably sized to confront the entire area where PDT is required. The LED lamp system and treatment surface are preferably arranged such that radiation is emitted toward the treatment area at sufficient proximity and intensity to achieve the desired treatment effect.

The device may be arranged to provide irradiation to a particular area of the inside of the orifice. Thus, the device may include a treatment surface arranged to direct and/or focus illumination onto a particular area of the inside of the orifice when the device is in use. In one preferred embodiment the device is adapted for use in PDT of the cervix. Therefore, preferably the treatment surface is shaped so as to cover, in use, the opening of the cervix. In this way, when the device is correctly inserted into the vagina the treatment surface will cover the opening of the cervix and hence enable the emitted light to irradiate the cervical area.

The size of this treatment surface should be such that it fits over the entire portio of the uterine cervix, e.g. 20-50 mm in diameter, more preferably 20-35 mm in diameter and most preferably 22-30 mm in diameter.

Preferably, the treatment surface is at least partially transparent so as to allow light from the LED to pass through the surface to provide the required PDT treatment or diagnosis. In some embodiments the treatment surface may be fully transparent to light having the wavelengths required for PDT treatment and being emitted by the at least one LED. However, preferably the material of the treatment surface and/or other material between the treatment surface and the light emitting portion(s) of the LED lamp system is arranged to diffuse the light, thereby enabling an even distribution of light from a number of LEDs. In one embodiment, a transparent material is used to form both the housing around the LED lamp system and also the treatment surface, thereby acting as both a housing for the lamp system and a diffuser for the light. In an alternative embodiment, a transparent material is used to form the treatment surface while a non transparent material is used to form the housing. This will ensure that only the area in need of treatment is illuminated while other areas which get in contact with the device are not subjected to irradiation. Preferably, a transparent silicone is used as a material for the treatment surface which acts as a diffuser for the emitted light.

In some preferred embodiments the at least one LED may be positioned on or extend out of the treatment surface. In such embodiments it is not necessary for the light to pass through the treatment surface and hence no constraints are placed on its opacity.

In one preferred embodiment the treatment surface is concave. This can assist in directing the emitted light towards a treatment area, such as the cervix.

In embodiments designed for providing irradiation to the cervix, the device comprises a protrusion which extends from the treatment surface. Preferably this protrusion forms a cylindrical tube. This can be used both to assist in the correct positioning of the device within the vagina and also to direct light to the cervical canal. In the latter case the tube acts as a light tube.

Preferably the flexible outer portion is located to the rear of the treatment surface. This prevents any interference with the radiation treatment. In preferred embodiments in which the outer portion is a continuous surface the outer portion can extend from the treatment surface towards to rear of the device, tapering outwards such that the widest section of the outer portion is located rearwards of the treatment surface.

The device comprises a LED lamp system which is capable of independent operation while the device is located within the orifice.

The lamp system may comprise one LED or preferably an array of LEDs. A particularly preferred LED array for PCT of cervix comprises 3-15 LEDs. The term "LED" is intended to cover any form of light emitting diode, for example OLEDs (organic light emitting diode).

The energy consumption per unit time of the LED lamp system should be such that the heating of tissue does not result in undue discomfort or damage to the patient. The irradiation will in general be applied at a dose level of 10 to 200 $J/cm^2$, for example at 50 $J/cm^2$. The LED lamp system is therefore preferably arranged to provide, in operation, a fluence rate in the range of 0.5-100 $mW/cm^2$, and most preferably in the range of 1-10 $mW/cm^2$. This low fluence rate results in the total dose being administered over a relatively long time period, e.g. several hours. As mentioned above this is beneficial both in terms of reduced discomfort to the patient and in the efficacy of the treatment.

The wavelength of light used for radiation may be selected to achieve an efficacious photodynamic effect and hence the LEDs are selected for their ability to emit wavelengths of light suitable for this effect. In one preferred embodiment the at least one LED emits, in use, light having wavelengths in the range of 300-800 nm, for example, the range 500-700 nm has been found to be particularly effective. It can be particularly important to include the wavelengths 630 and 690 nm. Therefore preferably the at least one LED emits, in use, light having wavelengths in the range of 630-690 nm. In a most preferred embodiment, especially if the device is used together with a composition comprising a photosensitizer precusor selected from 5-aminolevulinic acid or a derivative, e.g. an ester thereof, red light (600-670 nm) is used since light at this wavelength is known to penetrate well into tissue. In some embodiments the LED lamp system comprises filters to ensure that only light within a certain wavelength range, such as those mentioned above, is emitted from the device. The treatment surface may be designed such that only light having these preferred wavelengths is transmitted.

The power source preferably comprises one or more batteries. The batteries should preferably operate via electrochemical reactions using chemicals that are not too toxic for the patient should the device break or leak while within the body. Suitable batteries include lithium batteries or equivalent of sufficient capacity which may also be stored for up to 10 years. For example a ½ AA size $LiMnO_2$ battery may be used. The slow loss of charge and small size of lithium ion batteries makes them particularly suited for use as the power supply for the device. In order to increase the safety of the device, it is preferable that the power source is sealed within the housing. By sealed it is meant that the housing is fluid tight in use to prevent fluids leaking into or out of the device.

At its most basic the lamp system can simply comprise electrical connections for the power supply and an LED or LEDs. With this arrangement, immediately prior to insertion of the device the lamp system would be activated to switch on the one or more LEDs. The device would then be inserted into the orifice where the LED(s) will illuminate the treatment area until the device is removed or the power supply is depleted.

Activation of the lamp system may be triggered by a switch. In order to allow the device to be maintained sterile and to keep the power source and other elements of the device enclosed, the switch is preferably enclosed within the housing and arranged to be operated whilst sealed within the housing. The switch may be a mechanical switch located beneath a flexible part of the housing, with operation of the switch being permitted by the resilience of the flexible part. Alternatively the switch may be operated by means of an electrical or magnetic field transmitted through the housing. A magnetically operated switch may be implemented by the use of a magnet outside the housing to hold a 'normally closed' reed switch open. When the magnet is removed the reed switch will close and this can be used to activate the device.

In a simple system using just a power source and LED it is hard to control the dosage level, as the precise life and power output of the power supply will vary. In addition the illumination provided by the LED array will be constant. In order to avoid unacceptable heating of tissue, low intensity light is preferably used and it may also be beneficial for the device to be able to provide pulsed light.

Therefore preferably the lamp system further comprises a control circuit, such as a microcontroller or microprocessor, for regulating the irradiation provided by the at least one LED. The control circuit of the lamp system may be activated by a switch as described above. In a preferred embodiment the control circuit comprises a timer. The lamp system can then be programmed to begin illumination at a pre-determined time interval after activation. This ensures that sufficient time has passed from activation to the start of illumination. For example, in order to allow the absorption or build up of porphyrins a certain time is required after application of a photosensitiser or precursor drug. The length of illumination can also be strictly controlled as the control circuit can be arranged to switch off illumination after a pre-determined dosage time has elapsed. To allow further build-up of endogenous photo sensitizers (from precursors) after the first illumination, the device may repeat the illumination (re-PDT) after a certain period of time, e.g. 3 hours.

In addition the control circuit may be arranged to provide pulsed illumination. This can be achieved by providing a function generator within a microprocessor. As mentioned above, pulsed light is advantageous in ensuring that no unacceptable heating of tissue occurs. In addition, providing intervals in illumination enhances tissue oxygenation and the effect of PDT. Further it allows for the re-accumulation of endogenous porphyrins in surviving cells that can be treated with repeated illuminations. The frequency and length of the pulses can be chosen according to the requirements of the treatment regime and set within the control circuit.

In one embodiment, the control circuit can be programmed by the user. This enables the length, strength and illumination pattern to be adjusted to suit individual treatments. Suitable re-writable memory forms include EPROM, EEPROM, flash etc. However, the control circuit memory is preferably read only (ROM) and programmed at the time of manufacture.

Access to the control circuit could be achieved by means of a user interface on the device. By answering a series of questions the user can set the initial delay period, dosage duration, number and length of light pulses etc. The interface may be integral with the device. Thus, it may comprise small buttons that may be pressed with a suitable tool or reed switches. Each button or switch may activate a given pre-set condition such as light dose, intensity, pulsed/steady light, etc.

It is important that all the electrical components of the lamp system and power source are sealed within or to the housing during use. Therefore the control circuit should preferably be sealed within the housing. As mentioned previously the LED(s) could be positioned such that these protrude from the housing. However, preferably the LED lamp system is entirely sealed within the housing during use.

In some embodiments the user interface may be accessible through a flexible area of the housing. Alternatively the housing may comprise an sealable opening which provides access to the interface.

The provision of a user interface however increases the size of the lamp system, which may be undesirable in certain applications. Therefore, alternatively, the control circuit may comprise a receiver for connection to a remote terminal. In this way specific program commands can be communicated from the remote terminal, e.g. a computer, to the control circuit.

In some embodiments the receiver comprises an input port adapted for connection to a cable. In such embodiments the input port is suitably shaped to receive, for example, a USB or other male connector.

The input port must be sealed during use. Therefore the housing may comprise a plug for insertion into the port. Alternatively the housing may consist of two components which can be connected by means of, for example, screw threads, push or snap fit connection or bayonet fitting. The connection comprises seals in order to ensure that the control circuit is sealed within the housing during use.

Alternatively the program commands may be transmitted to the device by means of a wireless connection. For example, the receiver may be an infra-red or radio wave receiver. This has the advantage that a physical input port is not necessary and instead the control circuit can be permanently sealed within the housing.

Preferably the control circuit further comprises a feedback system. This enables the control circuit to make adjustments in the treatment program to account for deviations in expected LED performance.

For example, the feedback system may comprise a light monitor or other direct or indirect monitor to measure the light dose that has been given to the patient. In such systems the control circuit may be programmed to switch off the LED(s) after a pre-determined dosage has been reached rather than a pre-determined time.

Alternatively the dosimeter may override the timer in the event that the LEDs do not operate as expected. For example, if the power supply is faulty the output of the LEDs may be reduced. Therefore it will be necessary to continue illumination beyond the pre-determined time in order to obtain a complete dose. Conversely if the power output of the LEDs is stronger than anticipated the illumination can be stopped ahead of the pre-determined time interval, or the duration of each pulse can be shortened to prevent overheating of tissue.

Another optional feature of the control circuit is one or more performance indicator lights for informing a user whether the device has operated correctly or whether a fault has occurred. The control circuit may be arranged to provide a signal to the user when treatment is complete to indicate that the device can be removed. For example an acoustic and/or visual signal may be provided, such as an alarm sound and/or a light signal. Alternatively or in addition, a vibration could be used as the signal to indicate the end of the treatment. Typically the patient would be informed of the length of the treatment and so the signal can be used to confirm an expected end of the treatment and hence need not be overly intrusive.

Advantageously, as the control circuit may be used to turn off the LEDs at the end of the treatment cycle there is no great ill effect for the patient if the device remains inserted for longer than the treatment time. However, it is expected that patients will wish to know when treatment has ended and the device can be removed.

Preferably some or all of the above mentioned features of the control circuit are contained in a microprocessor.

Preferably the device further comprises a lens system arranged to provide homogenous illumination over the treatment area. The treatment surface may act as the lens system. For example, this surface may be formed of silicone or another material comprising surface elements for diffusing the light emitted by the LED(s).

In use the device is preferably placed into the orifice by a doctor, a nurse or another person with experience or education within relevant fields. However, patients might in some situations choose to insert the device themselves.

In one preferred embodiment the device comprises a handle at its rear end. The handle can be used by the patient or medical practitioner to firmly grip the device during insertion and removal.

The handle may be an elongate arm extending from the housing of the device. In a preferred embodiment however the handle is arcuate in shape as smooth edges will prevent the possibility of discomfort or damage to the patient. In some preferred embodiments, the arcuate handle is attached to the device at two or more points on the flexible outer portion. This is beneficial as, when the handle is grasped and pulled, the flexible outer portion will be pulled inwards, thus easing removal of the device. A similar effect can be achieved by attaching a string or cord to at least two positions on the outer portion, although this latter embodiment will not assist in insertion.

Therefore preferably the device further comprises a removal mechanism attached at two or more positions to the flexible outer portion and comprising a central gripping portion.

Another option is for the device to be placed (and removed) using a specific instrument, such as a pair of tweezers.

Advantageously, the device is designed for a single-use and for disposal after that single use. Preferably, the device includes one or more features that promote single-use and/or prevent repeat use. For example, the power source may be arranged to provide power that is only sufficient for a single-use, i.e. such that the power source is depleted after the required treatment is complete. The power source may be arranged so as not to be re-charged, and/or the control circuit may lack access to re-charge the power source. The control circuit may be arranged to prevent re-use by means of features of its programming and/or it may include a deactivation mechanism that destroys circuitry or software when triggered. To prevent patient interference when in use, the control circuit may also be arranged to selectively deactivate if interference is detected. By enforcing single use patient safety is improved and a strict control of sterility of the device is ensured.

The device of the present invention can be used to provide PDT according to the following method. Firstly a composition comprising a photosensitizer or precursor thereof is applied to the area to be treated by a physician, where applicable by using a specialised applicator, or the area of interest is treated by means of a systematically acting drug. Such a systematically acting drug may be supplied intravenously or orally, for example. The programmed device is then switched on and inserted. The patient can then immediately leave the medical facility and continue their normal daily routine while the treatment area is receiving illumination from the device. In this way treatment can occur over a prolonged period of time without inconvenience to the patient. This allows a low fluence rate to be used, increasing the efficacy of the treatment. After the treatment is complete the patients can either return to the medical institution for removal of the device or remove it themselves. The device can either be discarded or returned to the medical institution for disposal.

In a preferred embodiment the device of the present invention further comprises a drug delivery system. The drug delivery system may comprise a drug carrying area on the housing, such as a drug carrying area on the treatment surface. This might be a textured surface for carrying a composition of photosensitizer or precursor or the treatment surface itself without any further modifications may act as a drug delivering system. Alternatively, the drug delivery system may comprise a reservoir for housing a composition comprising a photosensitizer or precursor thereof (hereinafter "composition").

The advantage of this embodiment of the present invention is that the patient need not wait at the hospital for several hours between application of the composition and illumination, as is normal in existing PDT procedures. The device may automatically perform the illumination either immediately upon application or preferably at a later time. In addition, only one invasive procedure is required.

Optionally the drug delivery system further comprises a physical, mechanical or electrical system related to delivery. Such an optional system may include, for example, filters, membranes, one or more reservoirs arranged to deliver the photosensitizer or precursor based upon a preset plan for drug delivery or based on physical conditions, such as for example pH, osmolality, temperature, pressure, water content in the surroundings. However, the simplest and in most cases the most preferred drug delivery system is just a single drug carrying area for housing the composition, and in a most preferred embodiment, the drug delivery system is the treatment surface itself.

In this preferred embodiment the method of use is similar to that described above except that the composition is not applied to the treatment area in a separate procedure. Instead the composition is applied to the drug carrying area, e.g. the treatment surface, and is hence applied to the body upon insertion of the device into the orifice. Illumination is then conducted as described above.

The composition can be supplied together with the device. In such instances the drug delivery system, i.e. drag carrying area or reservoir, preferably treatment surface, may be supplied with a cover, such as a foil or cap, to seal the composition within the device until use. Prior to insertion the cover is removed so that the composition can be released. Alternatively the device can be supplied separately from the composition. This enables the physician to choose the optimal composition for a particular case and add this to the drug delivery system, i.e. drug carrying area or reservoir, preferably treatment surface, prior to insertion.

The composition to be used with the device, whether in a pre-filled device or applied to the device before use or applied to the treatment area separately, may comprise any suitable photosensitizer or precursor of a photosensitizer.

A range of photosensitizers are known in the scientific literature. As discussed above, one type of such compounds are compounds that per se are toxic to target cells or species or have light emitting properties when exposed to light. Such compounds have relatively large molecular weights and are often complex molecules like phthalocyanines, chlorines, porphyrins or psoralens. Another type of photosensitizers are compounds that not per se are toxic to light emitting, but form such active compounds in vivo. Such compounds—referred to herein as precursors—are typically 5-aminolevulinic acid (5-ALA) and derivatives of 5-ALA, like 5-ALA esters. Either type of compound can be used or supplied with the present device.

5-aminolevulinic acid (5-ALA) and its derivatives are amongst the most clinically useful precursors of photosensitizers known in the art. These compounds are converted in the body to protoporphyrin IX (PpIX), which is a photosensitizer that absorbs light and in contact with oxygen generates singlet oxygen. Singlet oxygen is extremely reactive and reacts fast with various cellular biomolecules resulting in cell death.

5-ALA and its derivatives are widely known and used in methods of photodynamic therapy (PDT) for the treatment of various abnormalities or disorders of the skin or other epithelial organs or mucosa, especially cancers or pre-cancerous lesions, as well as certain non-malignant lesions, e.g. skin diseases such as psoriasis, actinic keratosis (AK) and acne. 5-ALA (Levulan®, Dusa) and 5-ALA methyl ester (Metvix®, Galderma, Switzerland) are commercial therapeutic products for PDT treatment of actinic keratosis and basal cell carcinoma.

The use of 5-ALA and derivatives thereof, e.g. 5-ALA esters in PDT is well known in the scientific and patent literature (see, for example, WO 2006/051269, WO 2005/092838, WO 03/011265, WO 02/09690, WO 02/10120 and US 6034267). All such derivatives of 5-ALA and their pharmaceutically acceptable salts are suitable for use with the device herein described.

Esters of 5-aminolevulinic acid and N-substituted derivatives thereof are preferred precursors in a composition for use with the invention. Those compounds in which the 5-amino group is unsubstituted, i.e. the ALA esters, are particularly preferred. Such compounds are generally known and described in the literature (see, for example, WO 96/28412 and WO 02/10120 to Photocure ASA).

Esters of 5-aminolevulinic acid with substituted or unsubstituted, preferably substituted, alkanols, i.e. alkyl esters or, more preferably, substituted alkyl esters, are especially preferred precursors in a composition for use with the invention.

Examples of such precursors include those of formula (I) and pharmaceutically acceptable salts thereof:

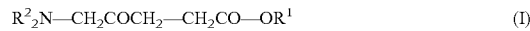

$$R^2{}_2N\text{—}CH_2COCH_2\text{—}CH_2CO\text{—}OR^1 \quad (I)$$

wherein
$R^1$ represents a substituted or unsubstituted alkyl group; and
$R^2$ each independently represents a hydrogen atom or a group $R^1$ As used herein, the term "alkyl", unless stated otherwise, includes any long or short chain, cyclic, straight-chained or branched saturated or unsaturated aliphatic hydrocarbon group. The unsaturated alkyl groups may be mono- or polyunsaturated and include both alkenyl and alkynyl groups. Unless stated otherwise, such alkyl groups may contain up to 40 carbon atoms. However, alkyl groups containing up to 30 carbon atoms, preferably up to 10, particularly preferably up to 8, especially preferably up to 6 carbon atoms are preferred.

In compounds of formula I, the $R^1$ groups are substituted or unsubstituted alkyl groups. If $R^1$ is a substituted alkyl group, one or more substituents are either attached to the alkyl group and/or interrupt the alkyl group. Suitable substituents that are attached to the alkyl group are those selected from: hydroxy, alkoxy, acyloxy, alkoxycarbonyloxy, amino, aryl, nitro, oxo, fluoro, —$SR_3$, —$NR^3{}_2$ and —$PR^3{}_2$, wherein $R^3$ is a hydrogen atom or a $C_{1-6}$ alkyl group. Suitable substituents that interrupted the alkyl group are those selected from: —O—, —$NR_3$—, —S— or —$PR_3$.

If $R^1$ is a substituted alkyl group, one or more aryl substituents, i.e. aryl groups, preferably one aryl group, are preferred.

As used herein, the term "aryl group" denotes an aromatic group which may or may not contain heteroatoms like nitrogen, oxygen or sulphur. Aryl groups which do not contain heteroatoms are preferred. Preferred aryl groups comprise up to 20 carbon atoms, more preferably up to 12 carbon atoms, for example, 10 or 6 carbon atoms. Preferred embodiments of aryl groups are phenyl and napthyl, especially phenyl. Further, the aryl group may optionally be substituted by one or more, more preferably one or two, substituents. Preferably, the aryl group is substituted at the meta or para position, most preferably the para position. Suitable substituents include halo alkyl, e.g. trifluoromethyl, alkoxy, preferably alkoxy groups containing 1 to 6 carbon atoms, halo, e.g. iodo, bromo, chloro or fluoro, preferably chloro and fluoro, nitro and $C_{1-6}$ alkyl, preferably $C_{1-4}$ alkyl. Preferred $C_{1-6}$ alkyl groups include methyl, isopropyl and t-butyl, particularly methyl. Particularly preferred aryl substituents are chloro and nitro. However, still more preferably the aryl group is unsubstituted.

Preferred such $R^1$ groups are benzyl, 4-isopropylbenzyl, 4-methylbenzyl, 2-methylbenzyl, 3-methylbenzyl, 4[t-butyl]benzyl, 4-[trifluoromethyl]benzyl, 4-methoxybenzyl, 3,4-[di-chloro]benzyl, 4-chlorobenzyl, 4-fluorobenzyl, 2-fluorobenzyl, 3-fluorobenzyl, 2,3,4,5,6-pentafluorobenzyl, 3-nitrobenzyl, 4-nitrobenzyl, 2-phenylethyl, 4-phenylbutyl, 3-pyridinyl-methyl, 4-diphenyl-methyl and benzyl-5-[(1-acetyloxyethoxy)-carbonyl]. More preferred such R1 groups are benzyl, 4-isopropylbenzyl, 4-methylbenzyl 4-nitrobenzyl and 4-chlorobenzyl. Most preferred is benzyl.

If $R^1$ is a substituted alkyl group, one or more oxo substituents are preferred. Preferably, such groups are straight-chained $C_{4-12}$ alkyl groups which are substituted by one, two or three oxo groups. Examples of such groups include 3,6-dioxa-1-octyl and 3,6,9-trioxa-1-decyl.

If $R^1$ is an unsubstituted alkyl group, $R^1$ groups that are saturated straight-chained or branched alkyl groups are preferred. If $R^1$ is a saturated straight-chained alkyl group, $C_{1-10}$ straight-chained alkyl group are preferred. Representative examples of suitable straight-chained alkyl groups include methyl, ethyl, n-propyl, n-butyl, n-pentyl, n-hexyl and n-octyl. Particularly preferred are $C_{1-6}$ straight-chained alkyl group, most particularly preferred methyl and n-hexyl. If $R^1$ is a saturated branched alkyl group, such branched alkyl groups preferably consists of a stem of 4 to 8, preferably 5 to 8 straight-chained carbon atoms which is branched by one or more $C_{1-6}$ alkyl groups, preferably $C_{1-2}$ alkyl groups. Examples of such saturated branched alkyl groups include 2-methylpentyl, 4-methylpentyl, 1-ethylbutyl and 3,3-dimethyl-1-butyl.

In compounds of formula I, each $R^2$ independently represents a hydrogen atom or a group $R^1$. Particularly preferred for use in the invention are those compounds of formula I in which at least one $R^2$ represents a hydrogen atom. In especially preferred compounds each $R^2$ represents a hydrogen atom.

The most preferred precursors to be used in a composition together with the devices according to the invention are compounds of formula I and pharmaceutically acceptable salts thereof, wherein $R^1$ is $C_1$-$C_6$ alkyl, e.g. hexyl, more preferably straight chain $C_1$-$C_6$ alkyl, e.g. n-hexyl and both $R^2$ represent hydrogen, i.e. 5-ALA hexyl ester and pharmaceutically acceptable salts thereof, preferably the HCl salts. The most preferred precursor is 5-ALA hexyl ester and the most preferred pharmaceutically acceptable salt of 5-ALA hexyl ester is the HCl salt.

The composition comprising the photosensitizer or precursor to be used together with the current device can be any type of pharmaceutical formulation and may be prepared by any conventional procedure available in the art (see WO 02/10120 to Photocure ASA). For example, esters of 5-ALA may be prepared by reaction of 5-ALA with the appropriate alcohol in the presence of base. Alternatively compounds for use in the invention may be available commercially (e.g. from Photocure ASA, Norway).

Preferred formulations are liquids (aqueous and non-aqueous), solids such as dusting powder, tablets or suppositories, semi-solids such as creams, ointments, gels or pastes, foam formulations or other expandable formulations (for example based on heating to body-temperature) and formulations/systems similar to patches. The components in the composition are the same components found in pharmaceutical products on the market, and a listing of such components can be found in handbooks of pharmaceutical excipients.

It is important that the formulation is a such that the composition is absorbed completely into the tissue to be treated or is transparent in order not to interfere with the illumination. As noted above, it is also possible to make use of compositions that are applied systematically, for example drugs that are given to the patient intravenously.

Viewed from another aspect the present invention provides a method of photodynamic therapy of a treatment area within an orifice of the body, the method comprising: applying a composition comprising a photosensitizer or precursor to the treatment area and inserting an irradiation device according to the present invention into the orifice, such that the LED lamp system of the irradiation device operates to provide illumination to the treatment area.

The method may include a step of selecting a device of suitable size and/or shape. The device may be selected firstly to suit the orifice concerned, and secondly to suit different patient conditions. For example, a device for treatment of the cervix would preferably be selected from a range of sizes depending on the patient's history of pregnancy.

The composition may be applied to the treatment area prior to insertion of the device, and this may be done by directly applying the composition, where applicable by using a suitable applicator, or by means of a systematically applied drug, for example a drug introduced intravenously into the patient. In an alternative preferred embodiment the composition is supplied via a drug delivery system of the device such that the steps of application of the composition and insertion of the device occur simultaneously. The drug delivery system may comprise a drug carrying area or reservoir or may simply be the treatment surface of the device, as discussed above.

Preferably the lamp system provides a dose level of 10 to 200 $J/cm^2$, for example 50 $J/cm^2$. The lamp system may have features as discussed above.

The device can be provided separately from the composition or with the composition already contained within a drug delivery system. Alternatively the device could be provided in the form of a kit comprising the device and at least one composition for use with the device.

The present device and method for photodynamic treatment may be combined with other therapeutic procedures, for example administration of other therapeutic drugs. These therapeutic drugs might be administered into the body prior to or together with placing the device in the orifice or might be administered through other routes of administration (e.g. oral, intravascular or dermal). Typically such drugs include hormones, antibacterial agents, antifungal agents, antiviral agents, anticancer agents or combination of such drugs.

Although some of the preferred features of the invention have been described in relation to providing PDT to the vagina and cervix, it will be appreciated that these features device could advantageously be included in devices for use in other body orifices, such as devices for the rectum, ear or nose, as discussed above. The present invention is not limited as to the particular orifice that it is to be used in, but instead the invention provides a device and method that can be beneficially used in the treatment of various conditions in different orifices.

Several preferred embodiments of the present invention will now be described, by way of example only, with reference to the accompanying drawings in which.

Figure 1A:
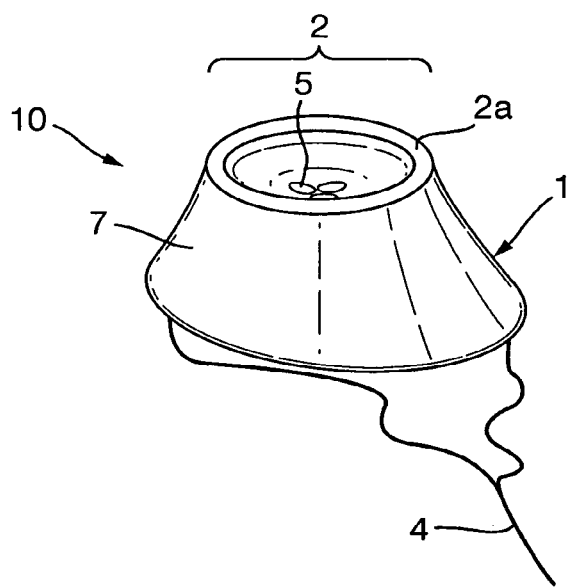
FIGS. 1A and 1B show a perspective view and cross-section respectively of a first preferred embodiment of an irradiation device.
Figure 1B:
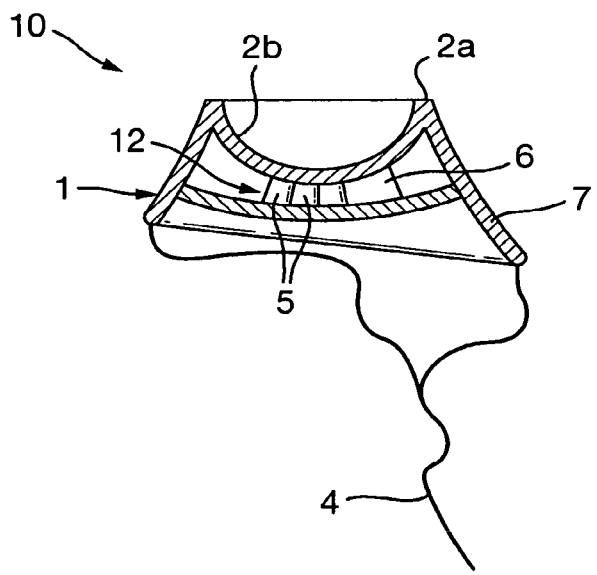

FIGS. 1A and B show a first embodiment of an irradiation device 10 for photodynamic therapy. The device 10 of the first embodiment is arranged for use in photodynamic treatment of the cervix. The device 10 comprises a flexible housing 1. The outer portion 7 of this housing is approximately frustoconical in shape and tapers outwards from the front end of the device to the rear. The outer portion 7 is resilient such that in use this presses against the walls of the vagina in order to securely hold the device 10 in place.

Sealed within the housing 1 is a lamp system 12. This system 12 comprises an array of LEDs 5 and a control circuit 6. This control circuit 6 will be discussed in more detail below. It provides power to the LEDs 5 such that, in use, these will illuminate the cervix.

The front end of housing 1 forms a treatment surface 2. This treatment surface 2 is shaped so as to cover, in use, the opening of the cervix, thus ensuring that the illumination from the LEDs 5 is directed on to the treatment area. Treatment surface 2 comprises a ring shaped contact surface 2a and a concave portion 2b. Typically the contact surface 2a has a diameter of 20 to 50 mm.

In order to assist in the removal of the device 10, a string 4 is attached to at least two positions on the outer portion 7. When the string 4 is grasped and pulled, the outer portion 7 is drawn inwards, hence easing the removal of the device 10.

Figure 2A:
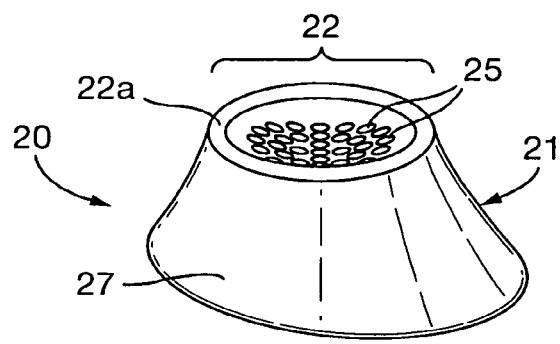
FIGS. 2A and 2B show a perspective view and cross-section respectively of a second preferred embodiment of an irradiation device.
Figure 2B:
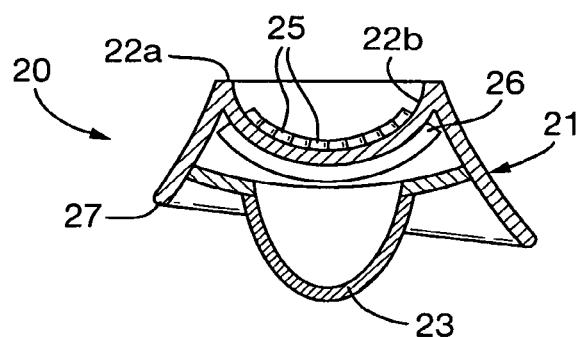

FIGS. 2A and 2B show an alternative embodiment of the device 20, which is also intended for use in the treatment of the cervix. In this embodiment, the device 20 again comprises a resilient outer portion 27 which is generally frustoconical in shape. In addition, the treatment surface 22 is again formed of a ring shaped contact surface 22a and a concave portion 22b. However, in this embodiment only the control circuit 26 is sealed within the housing 21. The LED array 25 protrudes into the concave portion 22b of contact surface 22.

Further, the device 20 comprises an arcuate handle 23 which extends from the rear end of the housing 21. Unlike the string used in the first embodiment, the handle 23 of device 20 can be used to assist in both the insertion and removal of the device.

Figure 3A:
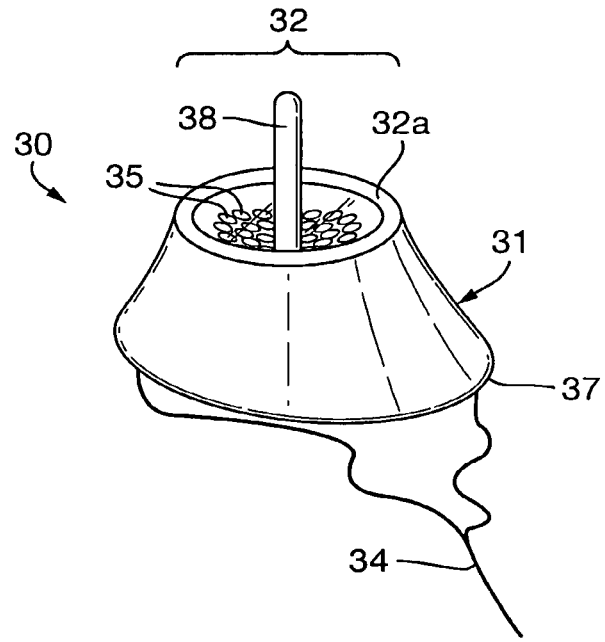
FIGS. 3A and 3B show a perspective view and cross-section respectively of a third preferred embodiment.
Figure 3B:
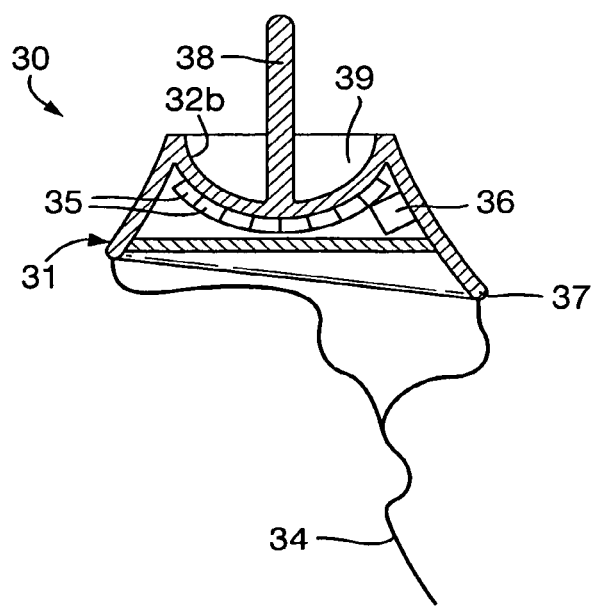

A third embodiment of the device 30 is shown in FIGS. 3A and 3B. Once again, the main shape of the housing 31 and the outer portion 37 remains unchanged.

The device 30 is similar in design to that of the device 10. Both the LED array 35 and the control circuit 36 are housed within housing 31 and a string 34 is provided to assist in the removal of the device 30.

However, two important differences exist. Firstly, a protrusion 38 extends from the treatment surface 32. This protrusion 38 forms a drug delivery system and light tube through which light from the LEDs 35 is directed. This protrusion 38 is shaped so as to contact, in use, the cervical canal. The tube allows the photosensitizer or precursor to be delivered to the cervical canal (endocervix) as well as the light from the LEDs 35 and therefore increases the ability of the device 30 to provide photodynamic therapy.

Further, the concave portion 32b of the treatment surface acts as a reservoir within which a treatment composition 39 can be housed. It can be seen that the concave portions 2b, 22b of the previous embodiments would also be suitable for housing this composition 39. In this way, the device of the present invention can also act as a drug delivery device. The composition 39 contains a photosensitizer or precursor suitable for photodynamic treatment or diagnosis. By placing this composition 39 within the device 10, 20, 30, the composition can be applied to the treatment area upon insertion of the device. In addition, delivery of the composition to the cervical canal can be obtained by also coating the protrusion 38 with the composition before inserting the device into the patient. In this way the patient need only undergo one invasive procedure before photodynamic treatment or diagnosis can be carried out.

Figure 4:
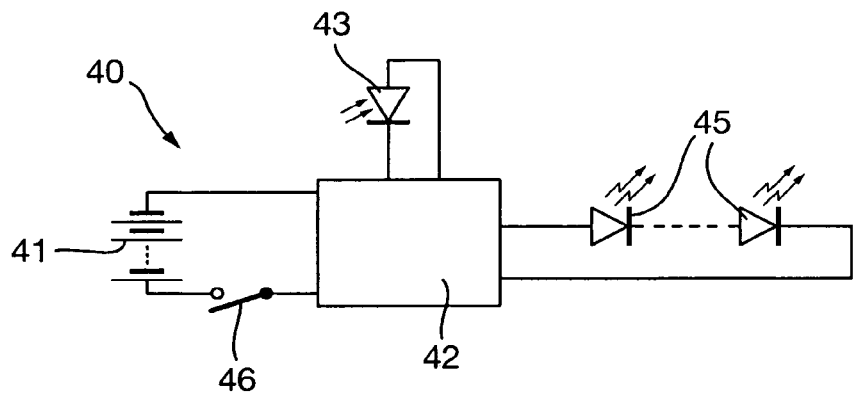
FIG. 4 shows a schematic diagram of a control circuit for use in the irradiation device of the preferred embodiments.

A control circuit suitable for use in any of the preferred embodiments of the irradiation device is shown in FIG. 4. This control circuit 40 takes power from lithium batteries 41 which are used to power the LED array 45. The control circuit 40 comprises a microprocessor 42, which controls the operation of the LED array 45.

For example, the microprocessor. 42 can comprise a timer and a memory into which can be programmed a dosage regime. The LED array 45 can therefore be operated to illuminate the treatment area for a predetermined length of time and can be arranged to operate continuously or provide pulsed illumination. In addition the control circuit 40 comprises a light sensor 43. This forms a feedback circuit which enables the microprocessor 42 to adjust the operation of the LEDs 45 to ensure that any abnormalities or malfunction of the control circuit 40 do not affect the dosage received by the patient.

Prior to the insertion of the device, a switch 46 is closed to begin operation of the control circuit 40. This may, for example, initiate timing of a "delay period", after which the microprocessor 42 will begin operation of the LED array 45 in accordance with the programmed regime. After a predetermined time, or upon completion of a certain light dose (determined by light sensor 43) the microprocessor 42 will switch off the LEDs 45. The device can then be removed.

In modified embodiments the control circuit also comprises two operation indicator lights (not shown). These may comprise two LEDs, one of which is illuminated if the device has operated correctly and a second LED which is illuminated if any malfunction has occurred; combinations of lights may indicate specific faults. Alternatively only a single operation indicator light may be provided, which is illuminated upon completion of correct operation of the device and which remains unlit if any malfunction has occurred. The control circuit may incorporate an alarm device for providing an audible signal, and/or a vibration device for providing a signal by vibration.

This system alerts the patient and the medical practitioner if any malfunction has occurred which has prevented the patient from receiving the correct dosage. Signals from the control circuit can also indicate that the treatment has been completed successfully.

Figure 5A:
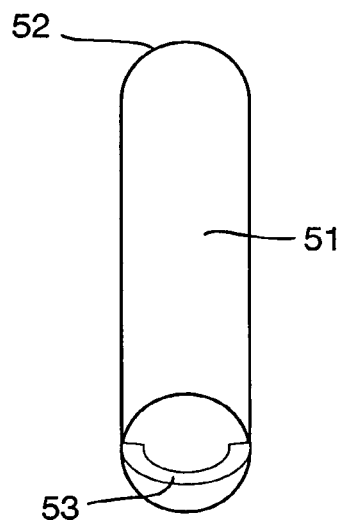
FIGS. 5A and 5B show an isometric perspective view and cross-section of a fourth preferred embodiment of an irradiation device.
Figure 5B:
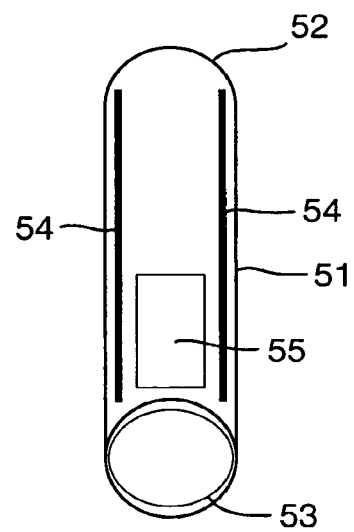

FIGS. 5A and 5B show a fourth embodiment of an irradiation device, and in this embodiment the device is arranged for treatment of the walls of an orifice of the human or animal body. The orifice could be, for example, the vagina, rectum, ear or nose. The particular size of the device and the specific shape can be varied in accordance with the size and shape of the orifice.

The device includes a housing 51 that encloses an array of LEDs 54 and a power supply and control circuit 55. The housing 51 of the illustrated embodiment is an elongate cylindrical shape with a hemispherical end 52. This shape is a preferred shape for insertion into the vagina and rectum, for insertion into other orifices, a conical end (not shown) could be used in place of the hemispherical end 52. A smaller device would be used for insertion into the nose and typically the shape would be adjusted to be more conical. For insertion into the ear a still smaller size and a slimmer shape would be used. At the opposite end to the hemispherical end 52 (or optional conical end) the device has a loop 53 to aid insertion and removal and to attach a string, if required.

The elongate cylindrical portion of the housing 51 includes a treatment surface about its outer circumferential surface. The treatment surface will contact the inside wall of the orifice in order to provide illumination to a treatment area on the orifice wall. To this end, the LED lamp system includes an array of LEDs 54 located about the elongate cylindrical portion beneath the treatment surface. The LEDs 54 are arranged to provide illumination through a cylindrical treatment surface. In modified embodiments, LEDs may also be located underneath a treatment surface of the hemispherical or conical end portion of the device. The housing 51 is made of transparent silicone, and this also forms the treatment surface which may also act as a drug delivery system. The transparent silicone acts as a lens that diffuses light emitted from the LED array and hence acts to evenly distribute the emitted light.

Figure 6A:
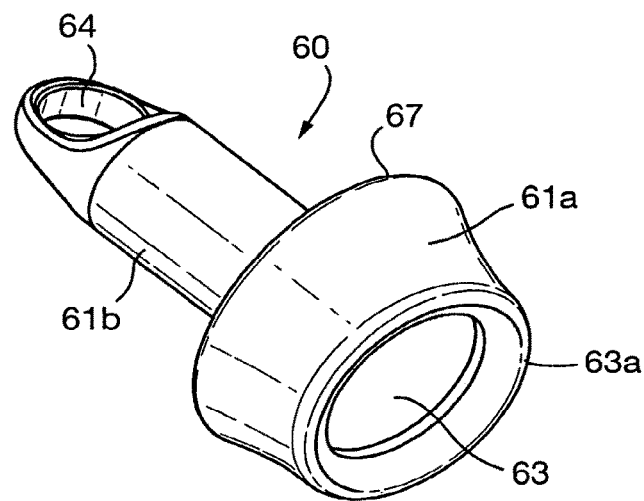
FIGS. 6A, 6B, 6C and 6D show a perspective view, side elevation, end elevation and cross-section view of a fifth preferred embodiment of an irradiation device.
Figure 6B:
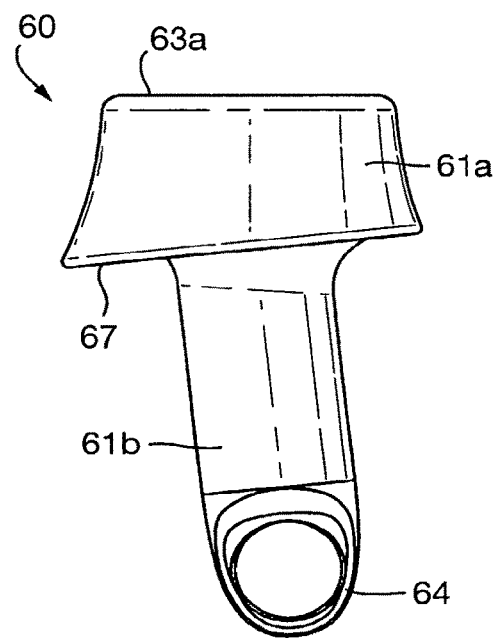
Figure 6C:
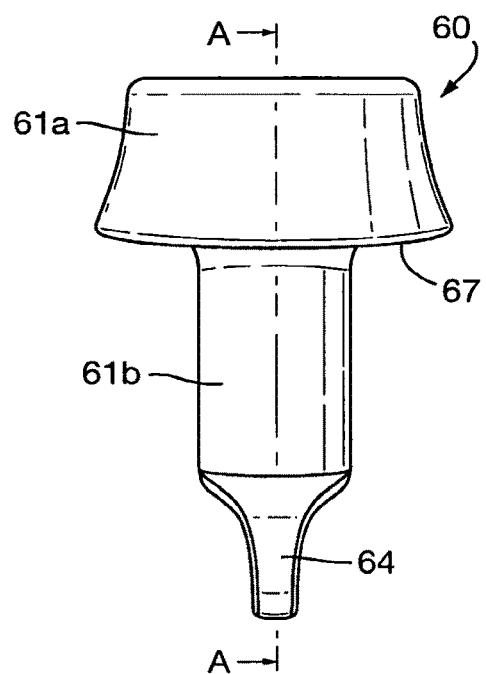
Figure 6D:
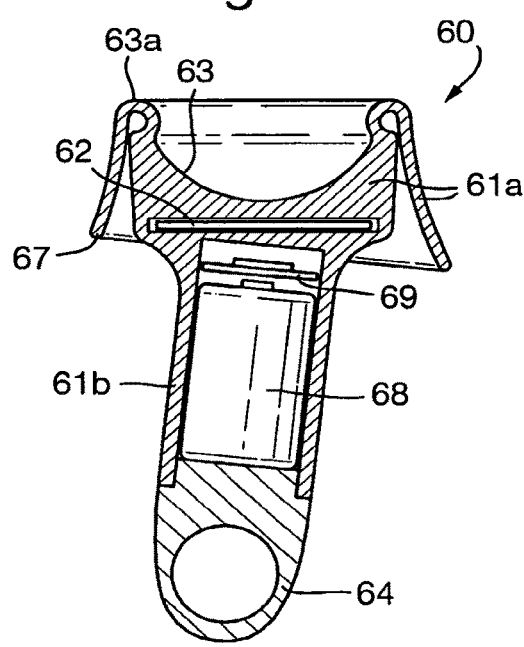

FIGS. 6A, 6B, 6C and 6D show a fifth embodiment of an irradiation device 60 for photodynamic therapy. FIG. 6D is a cross-section along line A-A on FIG. 6C. The device 60 of the fifth embodiment is arranged for use in photodynamic treatment of the cervix and has a housing 61 including an upper housing portion 61a with features similar to the first and second embodiments, with the addition of a lower cylindrical housing portion 61b extending beneath the upper housing portion. The upper housing portion 61a is flexible and includes an outer portion 67 that is approximately frustoconical in shape and tapers outwards from the front end of the device 60 to the rear. The outer portion 67 is resilient such that in use this presses against the walls of the vagina in order to securely hold the device 60 in place. The shape of the upper housing portion 61a and its outer portion 67 can most clearly be seen in FIG. 6D.

The LED lamp system 62 is sealed within the upper housing 61a, and has features similar to the embodiments discussed above. The power supply for the lamp system is a battery 68 enclosed within the cylindrical housing portion 61b. The battery is a ½ AA size battery with the cylindrical housing portion 61b formed relatively tightly around it. The control circuit 69 is also enclosed with the battery, and advantageously this takes the form of a PCB with a diameter the same as the battery diameter, for efficient use of space.

The front end of the upper housing 61a forms a treatment surface 63, which is a lens of transparent material covering the LEDs of the LED lamp system 62. As with the fourth embodiment, this material can be a transparent silicone which also forms the remainder of the flexible housing of the device 60. An opaque white silicone over-moulding can be used to cover the sides of the upper housing portion 61a, both about the outer portion 67 and also on the sides within the outer portion 67, and to completely cover the cylindrical portion 61b. This white over-moulding acts as a reflector for the lens of the treatment surface, and hides internal parts in the cylindrical portion, which would include the battery 68 and control circuit 69. In one embodiment, the underside surface of the housing portion 61a may be of black colour to protect the vaginal mucosa which is not in need of treatment against the emitted light.

The treatment surface 63 is shaped so as to cover, in use, the opening of the cervix, thus ensuring that the illumination from the LEDs is directed on to the treatment area. Treatment surface 63 comprises a contact surface 63a, which typically has a diameter of 22 to 30 mm. In a preferred embodiment, said contact surface 63a acts as a drug delivery system, i.e. drug carrying area or reservoir and carries a photosensitizer or a precursor.

At the base of the cylindrical housing portion 61b a loop 64 is provided to facilitate insertion and removal of the device. A string can be attached to the loop 64, if required. Alternatively, the loop 64 is missing and a string is attached directly to at least two portions on the cylindrical housing portion 61b (not shown).

Figure 7A:
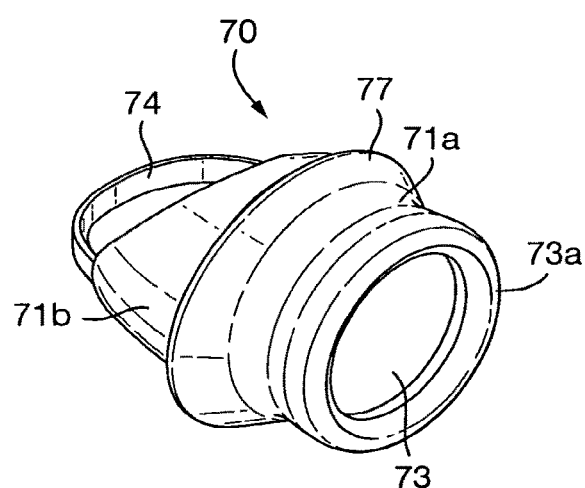
FIGS. 7A, 7B, 7C and 7D show a perspective view, side elevation, end elevation and cross-section view of a fifth preferred embodiment of an irradiation device.
Figure 7B:
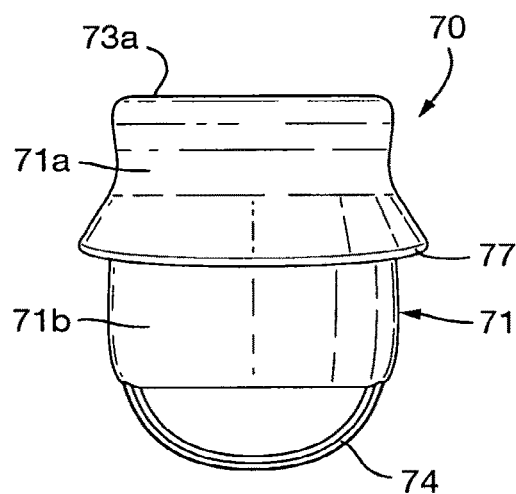
Figure 7C:
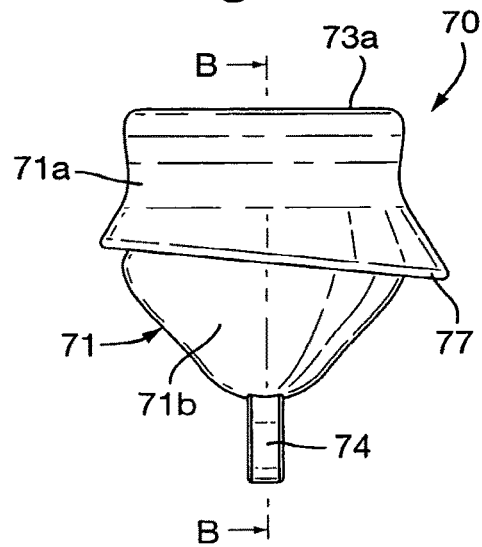
Figure 7D:
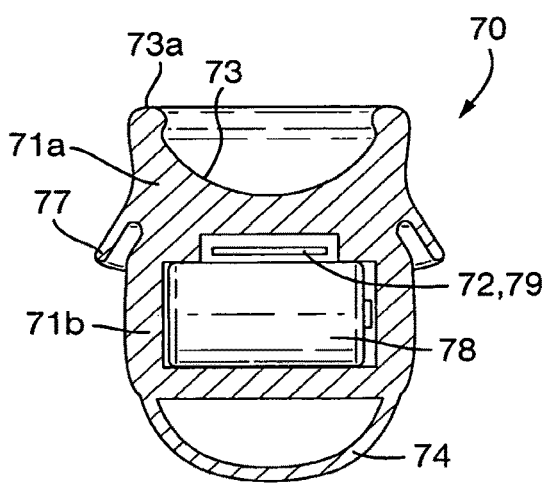

A sixth embodiment of the irradiation device 70, which is shown in FIGS. 7A, 7B, 7C and 7D. FIG. 7D is a cross-section along line B-B on FIG. 7C. Irradiation device 70 has a housing 71 consisting of an upper housing portion 71a and a lower housing portion 71b, wherein the upper housing portion 71a is similar to the upper housing portion 61a of the device 60 of the fifth embodiment. The upper portion 71a hence includes a generally frustoconical outer portion 77, with a treatment surface 73 formed by a contact portion 73a and a concave area within the truncated top of the frustoconical portion 77. The outer portion 77 of the sixth embodiment is shorter than the outer portion 67 of the fifth embodiment, which represents an alternative way of forming the device, and it should be appreciated that both of the fifth and the sixth embodiment could be adapted to use either the shorter or longer brim, each of which have different characteristics and advantages. A loop 74 is provided in the sixth embodiment in a similar fashion to the fourth and fifth embodiments. Alternatively, the loop 74 is missing and a string is attached directly to at least two portions on the lower housing portion 71b (not shown).

The lower cylindrical housing portion 61b of the sixth embodiment is replaced by an alternative lower housing portion 71b, which takes the form of a generally triangular prism with its long axis extending across a diameter of the upper portion 71a. The triangular prism is arranged to house a ½ size AA battery placed transversely across the device, instead of longitudinally in a cylindrical section as in the sixth embodiment. The edges of the prism are rounded for comfort. The control circuit 79 and LED lamp system 72 are both located above the battery 78.

As with the fifth embodiment, the sixth embodiment can include a white over-moulding to direct light to the treatment surface 73.

As discussed above, with a device intended for treatment of the cervix it is advantageous to provide different sizes since it allows effective treatment for patients with different histories of pregnancy. With the fifth and sixth embodiment, these different sizes can be realised by adjusting the size of the upper portions 61a, 71a, as these portions act to secure the device within the vagina with the treatment surface placed against the cervix. The lower portion 61b, 71b, which houses the power supply, can be manufactured in a single size, enabling a standardised arranged to be used for the battery 68, 78 and control circuitry 69, 79.

The photosensitising composition for the photodynamic therapy can be applied to the patient prior to insertion of the device, either directly to the surface of the treatment area, or systematically by intravenously or orally administered compositions. Preferably, the composition is applied to the treatment surface so that the photosensitising composition is applied to the patient during insertion of the device. With embodiments using a concave treatment surface, a photosensitive formulation may be placed within the concave area providing a reservoir of the formulation as discussed above. Alternatively, the material of the device may be selected so that the required photosensitive formulation will adhere to the treatment surface sufficiently for transfer to the patient and the formulation can then be simply applied in a layer on the treatment surface. For example, with the device of the fourth embodiment a formulation can be applied in a layer about the outside of the cylindrical housing.

As will be appreciated, the device of the present invention provides a convenient way for photodynamic therapy to be carried out in any orifice of the human or animal body over long time periods and at low fluence rates. This increases the convenience to the patient and, in some cases, the efficacy of the treatment.

The embodiments described above are for illustration only and should not be taken to limit the scope of protection. The skilled man will appreciate that adjustments could be made to these embodiments without deviating from the scope of the claims. For example, the housing may be any shape which allows full and secure insertion into the orifice and the exact shape of this housing will depend on whether the device is intended for use on a human or animal subject and on the orifice where the treatment is to occur. In addition other forms of control circuit and LED array can be used within the invention.

The invention claimed is:

1. An irradiation device for insertion into a vagina of a human and providing photodynamic therapy to a cervix of the human, the device having a front end and a rear end, the rear end being the part of the device which, in use, is closest to the entrance of the vagina and the front end of the device facing the cervix and comprising a front-facing treatment surface, wherein the device is adapted to be fully inserted and secured in the vagina with the front-facing treatment surface placed against the cervix, the device comprising:
    (a) a flexible housing comprising:
        (i) the front-facing treatment surface, which is placed against the cervix in use, said treatment surface is concave for complementary fit with the portio of the cervix and comprises an outer ring-shaped contact surface and an inner concave portion, wherein the outer ring-shaped contact surface has a diameter of 20 to 50 mm;
        (ii) a resilient outer portion forming a continuous surface which is frustoconical in shape and tapers outward from the ring-shaped contact surface towards the rear of the device such that the widest section of the resilient outer portion is located rearwards of the ring-shaped contact surface, wherein the resilient outer portion when in use adjusts its shape to form a secure fit within the walls of the vagina, and
        (iii) a housing portion that extends rearward of the resilient outer portion and has a smaller diameter than the resilient outer portion;
    (b) an LED lamp system comprising an array of LEDs located underneath the concave portion of the treatment surface and arranged to emit light having a wavelength of 500 to 700 nm with a light intensity of 1-50 mW/cm$^2$, when in use, through the concave portion of the treatment surface and onto the cervix;
    (c) a power supply for the LED lamp system enclosed in the housing;
    (d) a switch for activating the device that is enclosed within the housing and arranged to be operated whilst sealed within the housing; and
    (e) a timer, enclosed in the housing, which begins illumination by the array of LEDs a predetermined interval after activation of the switch;
wherein the device is independently operational while located in the vagina.

2. The device according to claim 1, wherein the flexible housing consists of a first and a second housing portion, the first housing portion comprising the treatment surface, the resilient outer portion and the LED lamp system and the second housing portion comprising the power supply.

3. The device as claimed in claim 1, wherein the light intensity is 1-10 mW/cm$^2$.

4. The device as claimed in claim 1, wherein the treatment surface is comprised of a material that diffuses the light emitted from the LEDs.

5. The device as claimed in claim 1, wherein the light emitted by the LEDs is regulated by a control circuit.

6. The device as claimed in claim 5, wherein the control circuit includes at least one of (a) a receiver for connection to a remote terminal, (b) a feedback system, or (c) one or more performance indicator lights for informing a user whether the device has operated correctly.

7. The device as claimed in claim 5, wherein the control circuit is programmed to provide pulsed illumination.

8. The device as claimed in claim 1, wherein the treatment surface includes a lens system arranged to provide homogenous illumination over the cervix.

9. The device as claimed in claim 1, wherein the device includes at least one feature that promotes single-use and/or prevents repeat use.

10. The device as claimed in claim 9, wherein the at least one feature is (a) the power source is arranged to provide power that is only sufficient for a single-use, (b) a control circuit is arranged to prevent re-use by means of features of its programming, or (c) a control circuit that includes a deactivation mechanism that destroys the circuitry or software, when triggered.

11. The device as claimed in claim 1, wherein the LEDs emit light with a wavelength in the range of 630-690 nm.

12. The device as claimed in claim 1, wherein the treatment surface acts as a drug delivery system and comprises, in use, a composition comprising a photosensitizer or precursor of a photosensitizer.

13. The device as claimed in claim 12, wherein the concave portion of the treatment surface acts as the drug delivery system and comprises, in use, the composition comprising the photosensitizer or precursor of the photo sensitizer.

14. The device as claimed in claim 13, wherein the composition comprises a 5-ALA ester or a pharmaceutically acceptable salt thereof.

15. The device as claimed in claim 14, wherein the composition comprises 5-ALA hexyl ester or a pharmaceutically acceptable salt thereof.

16. The device as claimed in claim 15, wherein the composition is a semi-solid or solid composition.

* * * * *